(12) United States Patent
Jung et al.

(10) Patent No.: US 12,357,095 B2
(45) Date of Patent: Jul. 15, 2025

(54) IMMERSIVE COUCH

(71) Applicant: SANGWHA CO., LTD., Seoul (KR)

(72) Inventors: Beom Joon Jung, Seoul (KR); Eun Giu Lee, Seoul (KR)

(73) Assignee: SANGWHA CO., LTD., Seoul (KR)

( * ) Notice: Subject to any disclaimer, the term of this patent is extended or adjusted under 35 U.S.C. 154(b) by 227 days.

(21) Appl. No.: 18/034,107

(22) PCT Filed: Oct. 29, 2021

(86) PCT No.: PCT/KR2021/015471
§ 371 (c)(1),
(2) Date: Apr. 27, 2023

(87) PCT Pub. No.: WO2022/092911
PCT Pub. Date: May 5, 2022

(65) Prior Publication Data
US 2023/0397737 A1   Dec. 14, 2023

(30) Foreign Application Priority Data

Oct. 30, 2020 (KR) ........................ 10-2020-0143654

(51) Int. Cl.
*A47C 4/54* (2006.01)
*A47C 1/024* (2006.01)
*A47C 1/032* (2006.01)
*A47C 3/025* (2006.01)
(Continued)

(52) U.S. Cl.
CPC .............. *A47C 4/54* (2013.01); *A47C 1/0242* (2013.01); *A47C 1/03211* (2013.01);
(Continued)

(58) Field of Classification Search
CPC ... A47C 15/004; A47C 3/0251; A47C 1/0242; A47C 1/03211; A47C 4/54; A47C 3/16; A47C 27/081; A47C 27/128
(Continued)

(56) References Cited

U.S. PATENT DOCUMENTS 3,708,204 A * 1/1973 Wachsmann ............. A47C 4/03
108/156
3,978,530 A * 9/1976 Amarantos .......... A47C 20/048
5/52
(Continued)

FOREIGN PATENT DOCUMENTS

JP    2012-514518     *   6/2012
KR    20120007930 U       11/2012
(Continued)

OTHER PUBLICATIONS

PDF of a machine English translation of the Written Opinion mailed Feb. 21, 2022 for PCT/KR2021/015471. (Year: 2022).*

*Primary Examiner* — Robert Canfield
(74) *Attorney, Agent, or Firm* — Bridgeway IP Law Group, PLLC; Jihun Kim

(57) ABSTRACT

An embodiment relates to an immersive couch, and more particularly to an immersive couch configured to be movable in three degrees of freedom using a concise and simple mechanism for moving an inflatable body, thereby not only improving convenience in use, safety, handling, storability, and maintainability, but also reducing manufacturing costs, operating costs, and maintenance costs. The immersive couch includes: a couch body formed as an inflatable body; a holding unit installed on the couch body; an actuation connecting member including one end connected to the holding unit; a rotary body connected to wind and unwind the actuation connecting member; a rotary body actuator rotating the rotary body forwards and backwards; and a controller controlling operations of the rotary body actuator.

7 Claims, 8 Drawing Sheets

(51) Int. Cl.
    *A47C 3/16*    (2006.01)
    *A47C 17/04*   (2006.01)
    *A47C 27/08*   (2006.01)
    *A47C 27/12*   (2006.01)
    *A63F 13/28*   (2014.01)
(52) U.S. Cl.
    CPC .............. *A47C 3/0251* (2018.08); *A47C 3/16* (2013.01); *A47C 27/081* (2013.01); *A47C 27/128* (2013.01); *A63F 13/28* (2014.09); *A63F 2300/1037* (2013.01)
(58) Field of Classification Search
    USPC ........................................ 297/217.3, 284.1
    See application file for complete search history.

(56) References Cited

U.S. PATENT DOCUMENTS

| | | | | |
|---|---|---|---|---|
| 12,201,224 | B2* | 1/2025 | Smit | ............... A47C 5/04 |
| 2009/0085393 | A1* | 4/2009 | Austen | ............... A47C 4/54 |
| | | | | 297/452.41 |
| 2011/0272989 | A1 | 11/2011 | Cho | |
| 2014/0021768 | A1* | 1/2014 | Chen | ............... A47C 4/54 |
| | | | | 297/452.41 |
| 2015/0250328 | A1* | 9/2015 | Brechet | ............... A47C 3/16 |
| | | | | 137/15.01 |
| 2022/0211178 | A1* | 7/2022 | Rowland | ............... A47C 1/143 |
| 2022/0361675 | A1* | 11/2022 | Smit | ............... A47C 3/029 |

FOREIGN PATENT DOCUMENTS

| | | |
|---|---|---|
| KR | 20-0469149 Y1 | 10/2013 |
| KR | 10-2015-0087163 A | 7/2015 |
| KR | 10-1880701 B1 | 7/2018 |
| KR | 10-2019-0119808 A | 10/2019 |
| KR | 10-2101607 B1 | 4/2020 |
| KR | 10-2020-0061975 A | 6/2020 |
| KR | 10-2170331 B1 | 10/2020 |
| WO | 2009061828 A1 | 5/2009 |
| WO | 2013153137 A1 | 10/2013 |

* cited by examiner

IMMERSIVE COUCH

TECHNICAL FIELD

The disclosure relates to an immersive couch, and more particularly to an immersive couch configured to be movable in three degrees of freedom using a concise and simple mechanism for moving an inflatable body, thereby not only improving convenience in use, safety, handling, storability, and maintainability, but also reducing manufacturing costs, operating costs, and maintenance costs.

BACKGROUND ART

A motion chair, generally called an immersive chair, a simulator, etc., has been actively applied to appreciation fields for various images such as a stereoscopic image in addition to simulation fields for games, driving, and the like.

Typically, such a motion chair includes a seat on which a user sits, a chair frame on which the seat is installed, and a motion actuator installed under the chair frame to perform three-degree-of-freedom movements.

As an example of the motion chair, a three-degree-of-freedom motion chair has been proposed in Korean Utility Model No. 20-0469149.

The three-degree-of-freedom motion chair disclosed in Korean Utility Model No. 20-0469149 includes first, second, and third up/down movable means 111, 112, and 113 at three positions under a chair frame 102 as shown in FIG. 1, in which the first, second, and third up/down movable means 111, 112, and 113 are respectively provided with motors M to implement the three-degree-of-freedom movements.

As described above, a conventional motion chair includes the plurality of movable means, the motors for actuating the movable means, and so on, thereby having drawbacks of not only structural complexity and expensiveness but also a high risk of negligent accidents such as being caught in the chair due to actuation based on a metal mechanism.

In addition, a conventional motion chair is too bulky and heavy to readily manufacture, install, move, use, etc. and is inconvenient to store and handle because it occupies too much space.

Further, a conventional motion chair not only excessively consumes electric energy because all movements, such as upward, downward, forward, backward, leftward, rightward and return movements are dependent on the actuating force of the motor, but also has disadvantages of high manufacturing costs and low productivity due to a complicated manufacturing process and many parts because a chair body and a cushion material are separately installed on a metallic chair frame during manufacturing.

Besides, a conventional motion chair has many failure points due to many parts and a complicated structure, thereby having a downside of increasing maintenance costs.

DISCLOSURE

Technical Problem

The disclosure is conceived based on the foregoing description, and an aspect of the disclosure is to provide an immersive couch configured to be movable in three degrees of freedom using a concise and simple mechanism for moving an inflatable body, thereby not only improving convenience in use, safety, handling, storability, and maintainability, but also reducing manufacturing costs, operating costs, and maintenance costs.

Technical Solution

According to an embodiment of the disclosure, an immersive couch includes: a couch body formed as an inflatable body; a holding unit installed on the couch body; an actuation connecting member including one end connected to the holding unit; a rotary body connected to wind and unwind the actuation connecting member; a rotary body actuator rotating the rotary body forwards and backwards; and a controller controlling operations of the rotary body actuator.

Further, the couch body may include a lower body seat allowing a lower body portion to be seated thereon, and a backrest allowing an upper body portion to be seated thereon, and the actuation connecting member may include a belt.

The rotary body actuator may include an actuation motor, and a reducer for reducing a rotational force of the actuation motor, and the rotary body may include a pulley connected to an output shaft of the reducer.

The immersive couch may further include an input unit for providing an input signal to the controller to operate the rotary body actuator.

Here, the input unit may include any one of a smartphone, a computer, a tablet computer, a game console, a smart television (TV), a set-top box, and a virtual reality head mounted display (VR HMD).

Further, the immersive couch may further include a human body information sensor installed in the couch body or the holding unit to detect body information of a human who is seated.

Meanwhile, the immersive couch may further include: an actuator housing in which the rotary body actuator and the rotary body are installed; and a supporting frame installed in the actuator housing.

Preferably, the actuator housing may include a lower housing in which the rotary body actuator and the controller are installed, and an upper housing coupled to an upper portion of the lower housing and formed with a moving hole through which the actuation connecting member moves.

The supporting frame may include a plurality of rod-shaped members installed in the lower housing.

The rotary body actuators may be installed to be positioned at rear left and right sides of the couch body to enable three-degree-of-freedom movements of the inflatable body, and the holding unit may include a planar body to be in close contact with the couch body, and a plurality of binding bands spaced apart from each other and installed in edges of the planar body so as to be bound to the actuation connecting member and the supporting frame.

The binding band may include front binding bands extended from front left and right sides of the planar body and bounded to the supporting frame, and rear binding bands extended from rear left and right sides of the planer body and bounded to the actuation connecting member.

The front binding band and the rear binding band may be formed as a band having an upper-wide and lower-narrow structure, of which a width becomes narrower from an upper portion connecting with the planar body toward a lower portion.

Advantageous Effects

In an immersive couch according to the disclosure, a couch body is provided as an inflatable body, and a pair of rotary body actuators are used to adjust ad control pulling and releasing distances, moving speed and acceleration, etc. of an actuation connecting member to effectively implement three-degree-of-freedom movements, thereby having effects on achieving a concise and simple structure, minimizing the volume and weight, improving convenience in use, safety, handling, storability, and maintainability, and reducing manufacturing costs, operating costs, and maintenance costs.

DESCRIPTION OF DRAWINGS

FIGS. 5A to 5C are views for describing major components of an immersive couch according to an embodiment of the disclosure, in which FIG. 5A is a perspective view of a couch body, FIG. 5B is a perspective view showing an assembled state of an actuator housing and a supporting frame, and FIG. 5C is a perspective view showing internal structure of an actuator housing, and FIGS. 6A and 6B are views for describing operations of an immersive couch according to an embodiment of the disclosure, in which FIG. 6A is a perspective view showing the operations of the immersive couch viewed from front, and FIG. 6B is a perspective view showing the operations of the immersive couch viewed from the top.

MODE FOR INVENTION

Below, embodiments of the disclosure will be described in more detail with reference to FIGS. 2 to 6B, in which like numerals in FIGS. 2 to 6B refer to like components. However, such embodiments are given for illustrative purposes only, and are not construed as limiting the scope of the disclosure.

Meanwhile, detailed descriptions about the configurations in the accompanying drawings and the operations and effects thereof, which can be easily understood by a person having ordinary knowledge in the art from general technology, will be simplified or omitted. Further, the disclosure is characterized in an immersive couch, and therefore the illustration and descriptions will be made focusing on parts related to such characteristics while simplifying or omitting the descriptions about the other parts.

Figure 1:
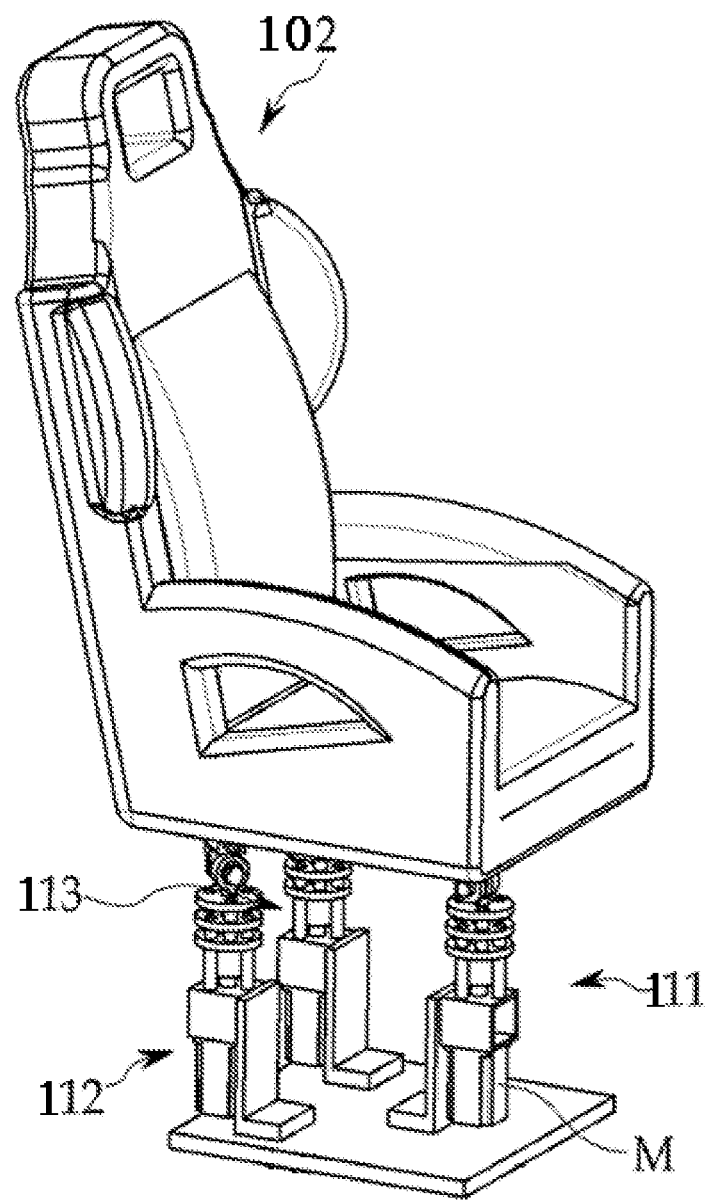
FIG. 1 is a view for describing a conventional motion chair.
Figure 2:
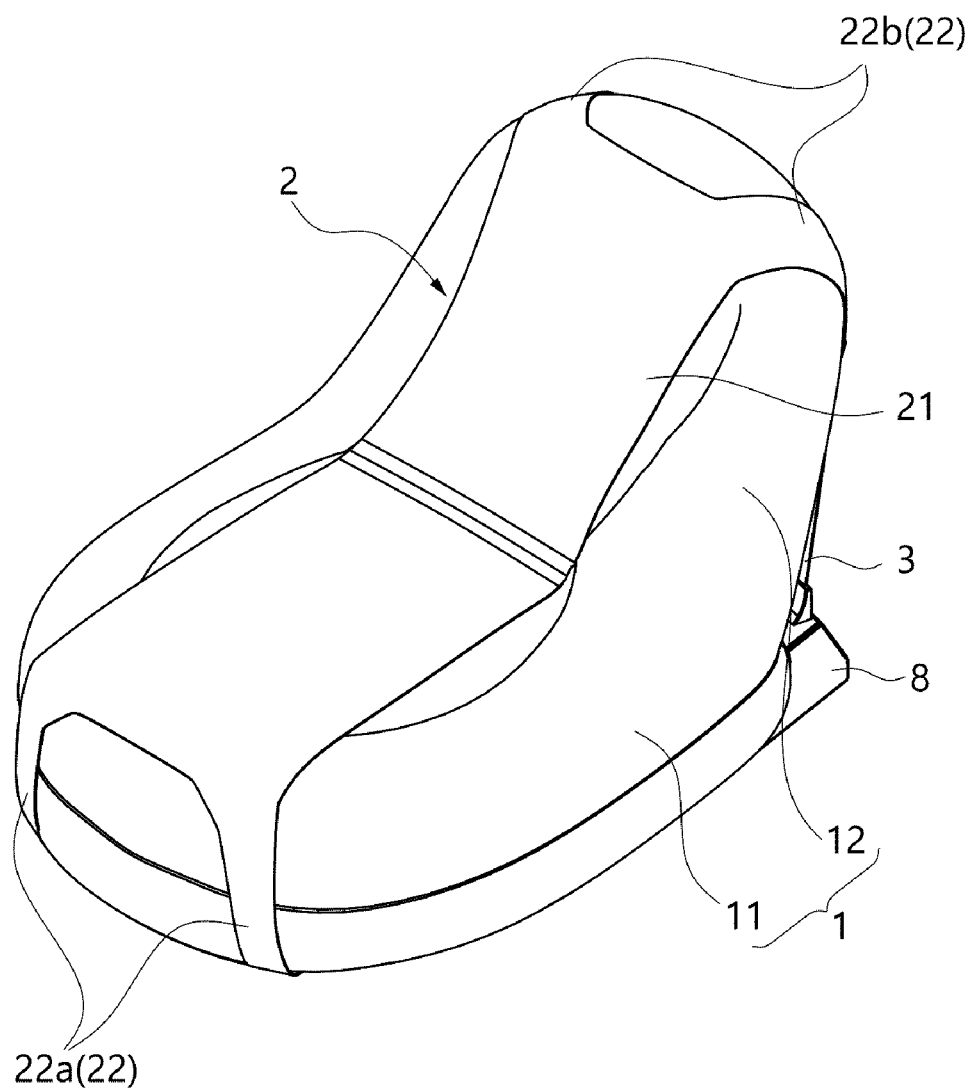
FIG. 2 is a perspective view of an immersive couch according to an embodiment of the disclosure viewed from the front.
Figure 3:
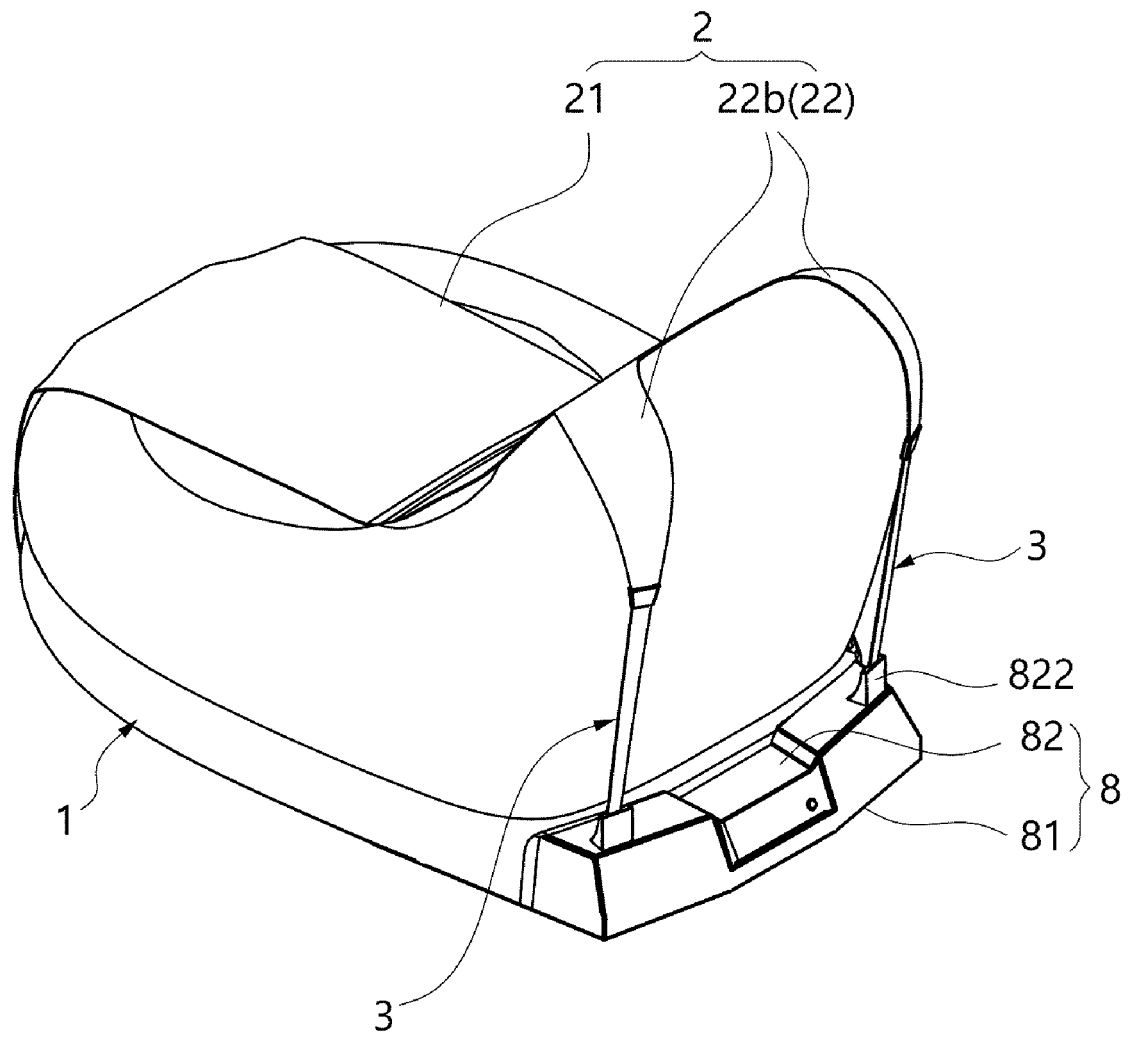
FIG. 3 is a perspective view of an immersive couch according to an embodiment of the disclosure viewed from the back of a couch body.
Figure 4:
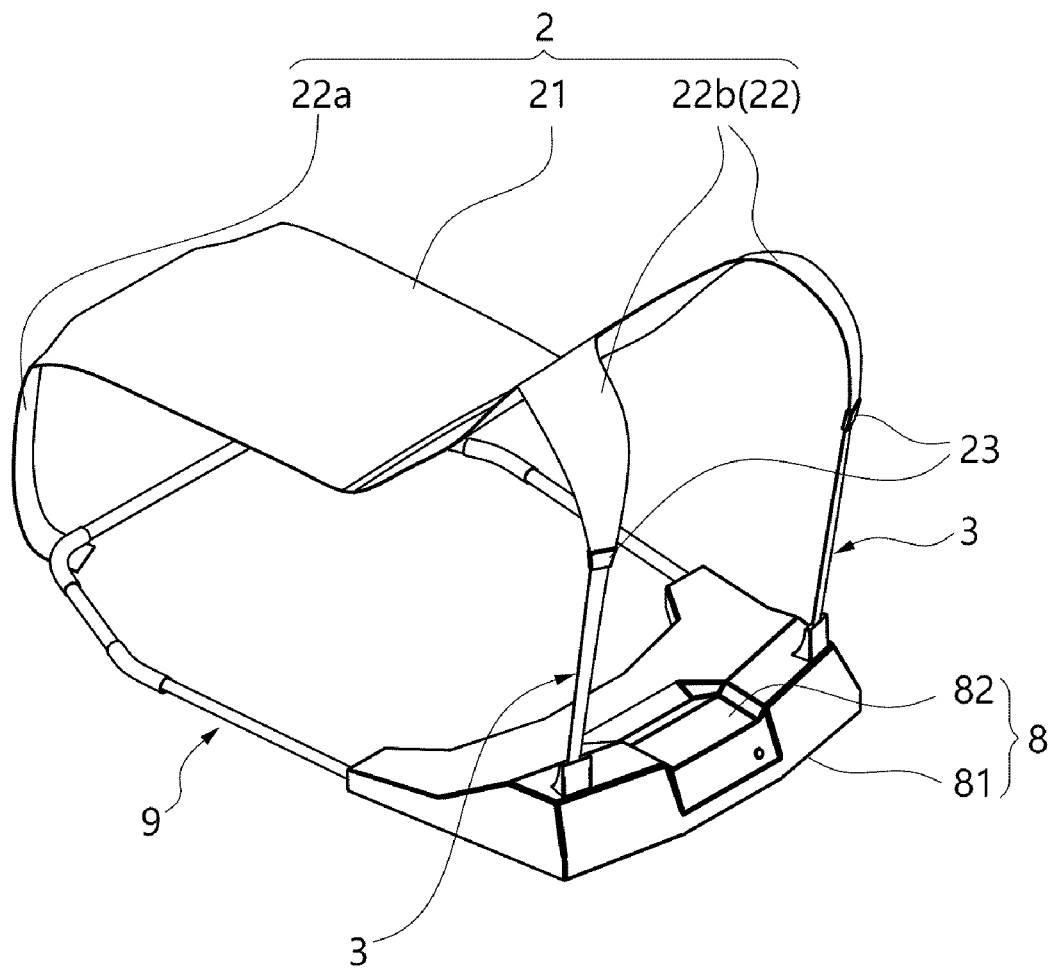
FIG. 4 is a perspective view showing components of an immersive couch according to an embodiment of the disclosure excluding a couch body.

FIG. 2 is a perspective view of an immersive couch according to an embodiment of the disclosure viewed from the front, FIG. 3 is a perspective view of an immersive couch according to an embodiment of the disclosure viewed from the back of a couch body, and FIG. 4 is a perspective view showing components of an immersive couch according to an embodiment of the disclosure excluding a couch body.

Referring to FIGS. 2 to 4, an immersive couch according to an embodiment of the disclosure is configured with a concise and simple structure to enable three-degree-of-freedom movements in response to an input signal such as various video and audio signals, and includes a couch body 1, a holding unit 2, an actuation connecting member 3, a rotary body 4, a rotary body actuator 5, an input unit (not shown), and a controller 7.

The couch body 1 according to an embodiment is formed as an inflatable body for contacting and expanding to enable three-degree-of-freedom movements and reducing its volume as necessary, but may be configured as various types of chairs without any specific limitation as long as a user can sit or lie thereon.

The couch body 1 is formed with planar sheets made of an airtight material to have an air injection chamber therein, and includes an air injection valve (not shown) for injecting and exhausting air. Here, the air injection valve may be selected among publicly known air injection valves through which air flows in and out, and therefore detailed descriptions thereof will be omitted.

Figure 5A:
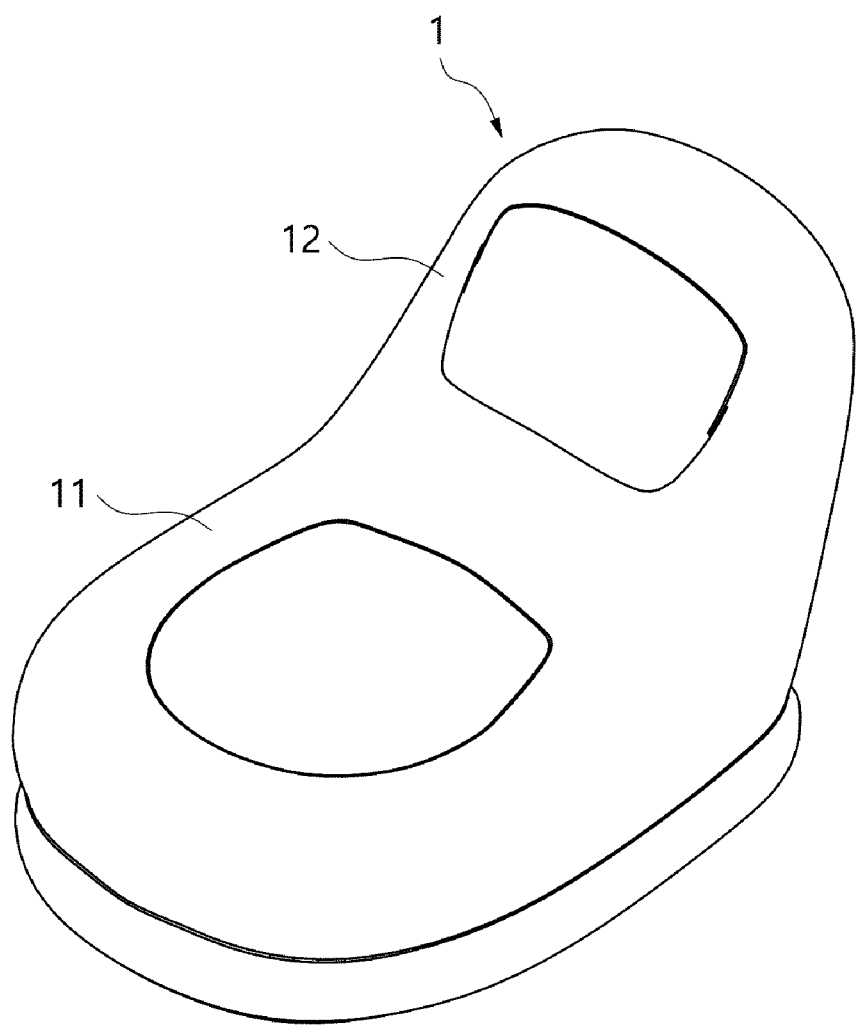

Further, the couch body 1 is approximately shaped like a sofa for one person while it is inflated, and, as shown in FIG. 5A, includes a lower body seat 11 allowing a user's lower body to be seated thereon, and a backrest 12 connected to the lower body seat 11 and allowing the user's upper body to be seated thereon.

The holding unit 2 refers to a component installed to come into close contact with the lower body seat 11 and the backrest 12 so that the couch body 1 can move more effectively, and functions to transfer the actuating force from the actuation connecting member 3 connected thereto to the couch body 1.

Preferably, the holding unit 2 includes a planar body 21 to be in close contact with the couch body 1, and a binding band 22 formed being extended from the edge of the planar body 21.

The planar body 21 may be made of various planar materials such as natural textile fabrics, artificial textile fabrics, natural leather, and artificial leather, without particular limitation, and is approximately shaped like a rectangle.

The plurality of binding bands 22 are formed at the edge of the planar body so as to be bound to the actuation connecting member 3 and a supporting frame 9 (to be described later). Preferably, the binding band 22 includes front binding band 22a extended from front left and right sides of the planar body 21 and bound to the supporting frame 9, and a rear binding band 22b extended from rear left and right sides of the planar body 21 and bound to the actuation connecting member 3.

In addition, the rear binding band 22b is provided with a binding unit 23 at a lower end thereof, to which the actuation connecting member 3 is bound. In this case, various types of buckles for binding and releasing a belt-type member may be applied to the binding unit 23. Further, although it is not shown, the front binding band 22a may also be provided with a VELCRO® fastener, a buckle, a hook, and the like binding unit.

Preferably, the binding band 22 is formed as a band, the width of which becomes narrower from an upper portion to be connected to the planer body 21 toward a lower portion, i.e., has a structure of which the upper portion is wide and the lower portion is narrow, thereby enhancing the close contact with the couch body 1, preventing the couch body from damage, and improving aesthetics.

The actuation connecting member 3 refers to a member for receiving the actuating force from the rotary body 4 and performing a function to move the couch body, and includes a first end bound to the holding unit 2 and a second end fastened to and wound around the rotary body 4. Here, the free end of the actuation connecting member 3, which is extended from the rotary body 4, is bounded to the binding unit of the rear binding band 22b, but may be integrally coupled to the rear binding band 22b by sewing when the rear binding band 22b does not include the binding unit.

In addition, the actuation connecting member 3 according to an embodiment is provided as a belt to stably transmit the actuating force, prevent negligent accidents, and improve aesthetics, but may be provided as a rope, a wire, and the like string material. Here, the belt may include a belt woven with a fabric yarn such as Kevlar® yarn and aramid yarn, which are known for high tension.

Figure 5B:
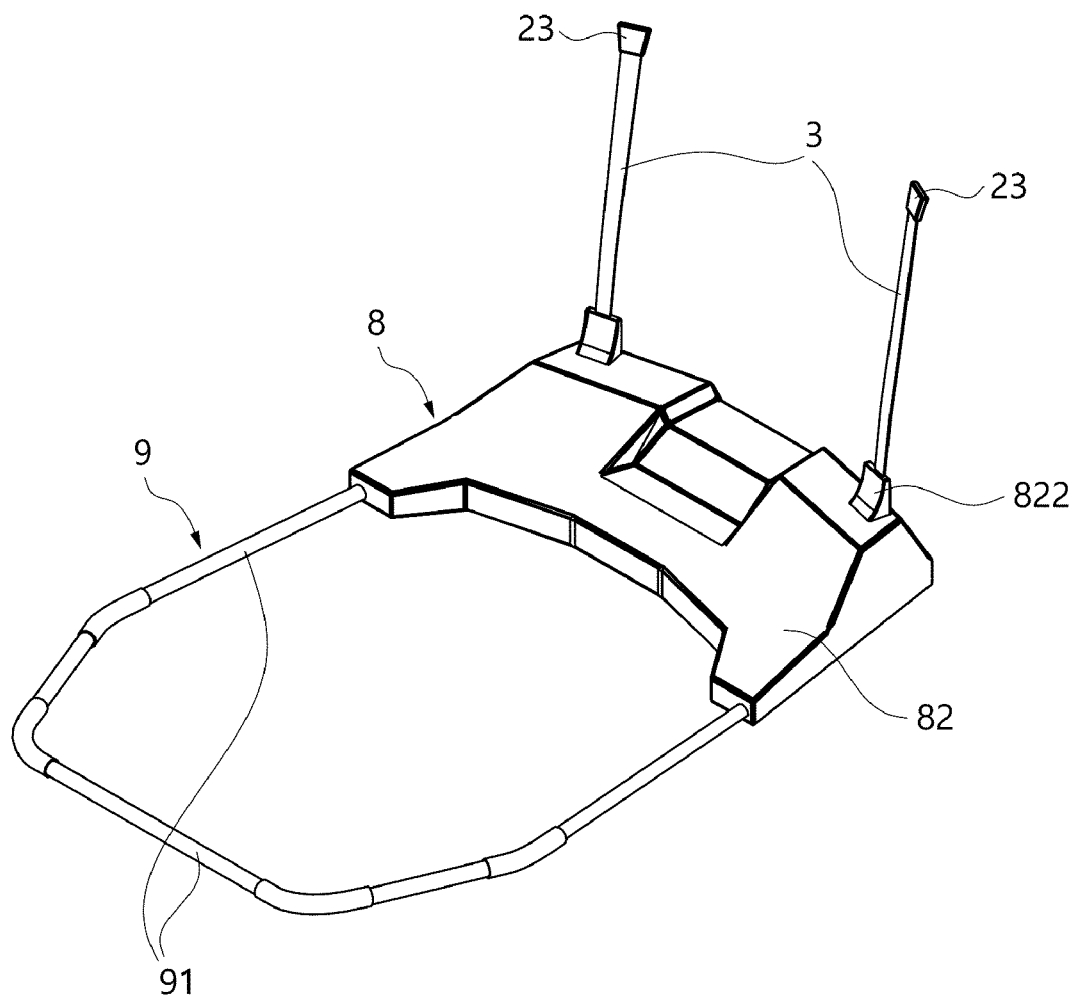
Figure 5C:
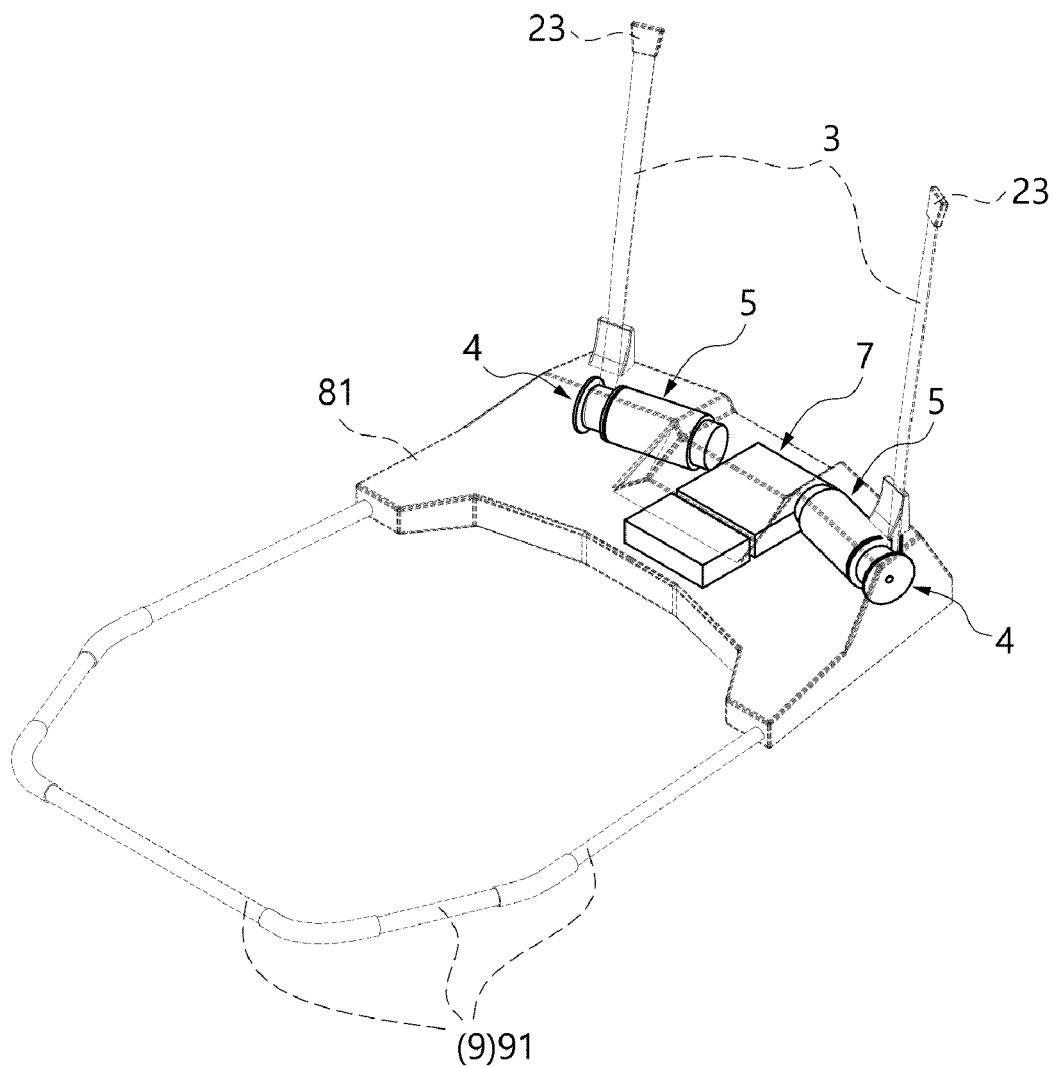

FIGS. 5A to 5C are views for describing major components of an immersive couch according to an embodiment of the disclosure, in which FIG. 5A is a perspective view of a couch body, FIG. 5B is a perspective view showing an assembled state of an actuator housing and a supporting frame, and FIG. 5C is a perspective view showing internal structure of an actuator housing. For ease of understanding, the rotary body 4, the rotary body actuator 5, and the controller 7, which are accommodated inside are illustrated with solid lines, and the other components are illustrated with broken lines.

Referring to FIG. 5C, the rotary body 4 refers to a component to be rotated by the actuating force of the rotary body actuator 5, and is formed as a pulley on which the actuation connecting member 3 is wound and unwound.

The pulley is connected to an output shaft of the rotary body actuator 5, and is recessed on an outer circumferential surface of a circular pulley body thereof to have a groove, the depth of which corresponds to the width and winding numbers of the actuation connecting member 3 provided as the belt.

The rotary body actuator 5 refers to a component for rotating the rotary body 4 forward and backward, and includes an actuation motor and a reducer for reducing the rotational force of the actuation motor.

In addition, the rotary body actuator 5 and the rotary body 4 may form a pair to implement three-degree-of-freedom movements such as roll, pitch, yaw, heave, sway and surge movements based on freely transformable characteristics of the inflatable body. Preferably, the rotary body actuators 5 are installed in an actuator housing 8 (to be described later) and spaced apart from each other so that the actuation connecting members 3 can be positioned at rear left and right sides of the couch body 1.

The input unit (not shown) refers to a component for providing an input signal to operate the rotary body actuator 5, and may be provided without limitation as long as it can provide a video signal, an audio signal, and the like for operating the rotary body actuator to the controller through a communicator (not shown) and a connection terminal (not shown) provided in the actuator housing 8.

For example, the input unit may include a smartphone, a computer, a tablet computer, a game console, a smart TV, a set-top box, a virtual reality head mounted display (VR HMD), etc.

The communicator may use wireless communication based on various near field communication technologies such as Wi-Fi®, infrared communication, and Bluetooth®, and Zigbee®, or wired communication based on a local area network (LAN) cable.

The controller 7 refers to a component for controlling the rotary body actuator 5 to operate based on the input signal of the input unit, and is provided as a control module including a microcomputer loaded with a program, and a printed circuit board mounted with various electric and electronic devices and circuits. The controller 7 is installed inside the actuator housing 8 (to be described later). Further, the controller 7 may include a publicly known motion controller applied to the field of motion chairs and the like to perform a function for controlling motion types according to input signals. Here, the motion types refer to various types of motions that can be implemented by the couch body, and are used for controlling the movements of the couch body, such as movement direction, movement angle, the speed and acceleration of the movement, etc. during the three-degree-of-freedom movements.

Meanwhile, the immersive couch according to an embodiment of the disclosure further includes the actuator housing 8 and the supporting frame 9 for structural safety and operational stability.

The actuator housing 8 refers to a component serving as a base on which the rotary body actuator 5 and the rotary body 4 are installed, and includes a lower housing 81, and an upper housing 82.

The lower housing 81 is disposed at a lower side, and includes a lower housing body on which the rotary body actuator 5 and the controller 7 are put and installed. The lower housing body includes fitting holes at opposite sides thereof to which the supporting frames 9 are fitted and assembled.

The upper housing 82 includes an upper housing body shaped corresponding to the lower housing 81 and coupled to an upper portion of the lower housing 81. The upper housing body includes a protruding portion 822 formed with a moving hole through which the actuation connecting member 3 moves.

The supporting frame 9 refers to a component provided to stably support the couch body 1 at a lower side, and is installed in the actuator housing 8.

Further, the supporting frame 9 according to an embodiment includes a rod-shaped member 91 installed to form a closed loop (or an approximately elliptical structure) in the lower housing 81, but the structure or shape thereof is not limited as long as it can stably support the couch body 1. Preferably, the supporting frame 9 is provided as a plurality of rod-shaped members to be easily assembled and disassembled and minimize the volume during handling such as storage and carriage.

Meanwhile, the immersive couch according to an embodiment of the disclosure may include a human body information sensor (not shown) installed in the couch body 1 and detecting body information of a user who sits on the couch body 1.

The human body information sensor may representatively include a weight sensor or a pressure sensor to detect the presence, weight, etc. of a user.

The human body information sensor may detect the weight and the like of a user and transmits it to the controller, thereby controlling the actuation of the rotary body actuator 5. For example, when the weight is not detected by the human body information sensor for a predetermined period of time or more, the actuation of the rotary body actuator 5 is stopped, thereby preventing negligent accidents and saving electric energy.

In addition, the human body information sensor may further include a biometric sensor to detect body temperature, blood pressure, heart rate, etc. Based on a detection signal from the biometric sensor, the actuation of the rotary body actuator 5 is adjusted in detail (e.g., adjusted in the strength of the three-degree-of-freedom movements) and diversified according to conditions of a user under control of the controller, thereby increasing satisfaction of a user (or a customer).

Below, the operations of the immersive couch according to an embodiment of the disclosure will be described in brief.

Figure 6A:
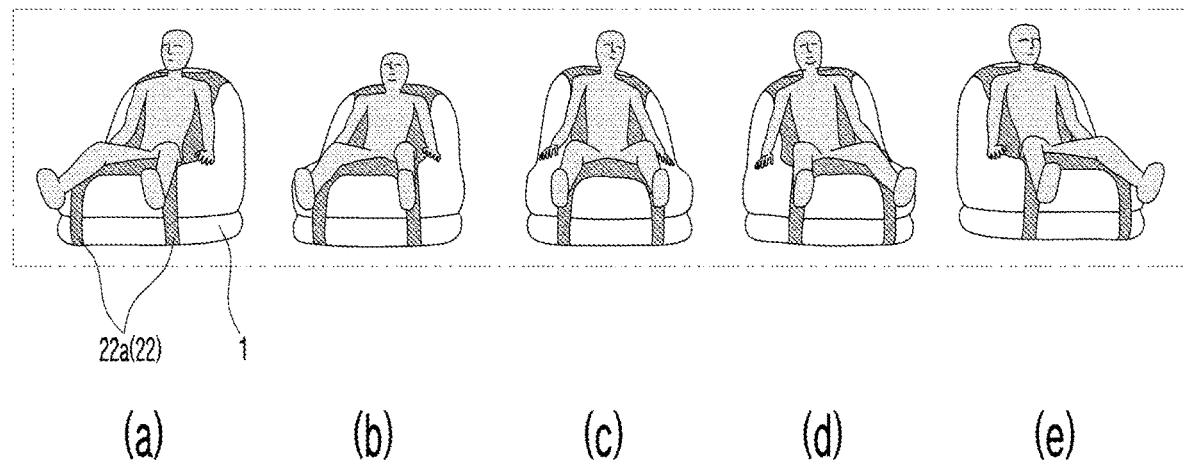
Figure 6B:
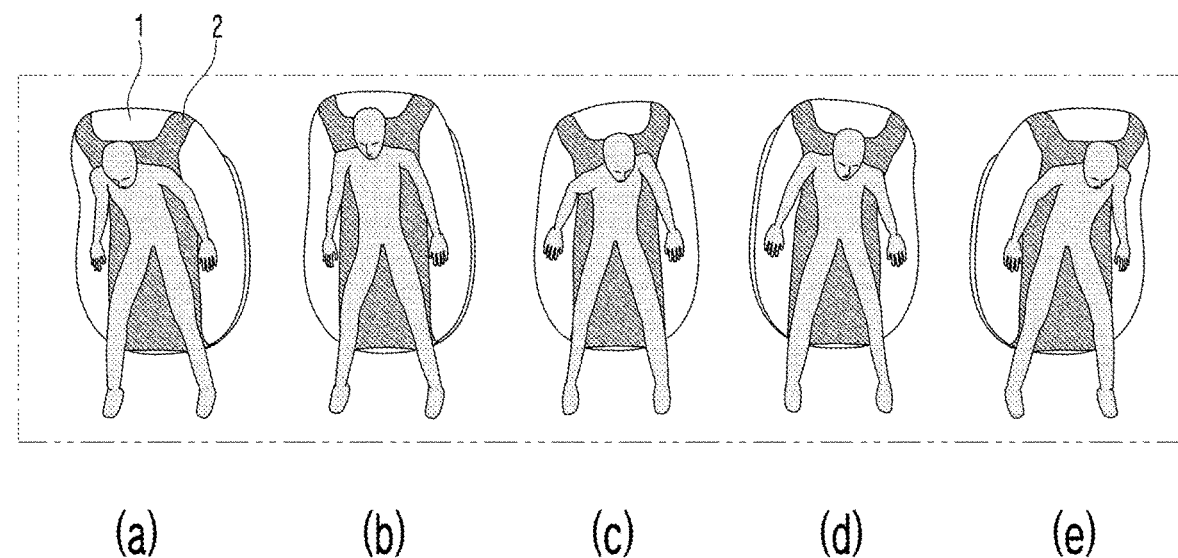

FIGS. 6A and 6B are views for describing operations of an immersive couch according to an embodiment of the disclosure, in which FIG. 6A is a perspective view showing the operations of the immersive couch viewed from front, and FIG. 6B is a perspective view showing the operations of the immersive couch viewed from the top.

Referring to FIGS. 2 and 5C, a schematic assembling process of the immersive couch according to an embodiment of the disclosure is as follows. The couch body 1 having the lower body seat 11 and the backrest 12 is formed by injecting air into the inflatable body of the couch body 1.

Then, the supporting frame 9 including the rod-shaped member 91 is assembled to the actuator housing 8 in which the rotary body 4 connecting with the actuation connecting member 3, the rotary body actuator 5 and the controller 7 have been assembled in advance. The couch body 1 is put on the supporting frame 9 assembled as above, and covered with the holding unit 2.

The holding unit 2 is assembled in such a way that the front binding bands 22a being spaced apart from each other are bound to the front left and right rod-shaped members 91 of the supporting frame 9, and the free ends of the actuation connecting members 3 are bound to the binding units of the rear binding bands 22b while the planar body 21 is disposed being put on the lower body seat 11 and the backrest 12.

The use of the immersive couch assembled as described above will be described below in short. When the controller receives an input signal from a smartphone, a computer, a tablet computer, a game console, a smart TV, a set-top box, a VR HMD, or the like input unit while a user is sitting on the couch body 1, corresponding actuation signals are transmitted to the two rotary body actuators 5 under control of the controller.

Therefore, each rotary body actuator 5 rotates the pulley of the rotary body 4 based on the rotational force of the actuation motor reduced into a predetermined reduction ratio by the reducer.

As the rotary body 4 rotates, the actuation connecting member 3 is unwound and wound to be changed in length, thereby transmitting the operational force to the couch body 1 through the rear binding band 22b.

In this case, the rotary body actuators 5 are spaced part from each other at the rear left and right sides of the couch body 1 and operate independently of each other, so that the actuation connecting members 3 can be different in length change and movement speed from each other, thereby implementing three-degree-of-freedom movements such as roll, pitch, yaw, heave, sway and surge movements.

The foregoing movements will be described in more detail with reference to FIGS. 6A and 6B. In a basic posture (a) where a user is seated, the two rotary body actuators 5 are differently operated under control of the controller to adjust the length, speed, acceleration, etc. of the actuation connecting member 3 being unwound and wound, thereby implementing the operations of the couch body 1 leaning backwards (b), leaning leftwards and rotating leftwards (c), leaning rightwards and rotating rightwards (d), and leaning forwards (e).

Further, the three-degree-of-freedom movements of the couch body 1 by the rotary body actuator 5 may implement various and realistic motions for movies or games, such as a motion based on continuous real-time information of the movie, the game or the like provided from the input unit to the controller, and motions and haptic responses prepared in advance and immediately performed by a motion controller when the decibel and pattern of a specific wavelength of a sound for the movie, the game, or the like provided from the input unit to the controller are normalized and the corresponding sound is output.

Although the configurations and operations of an immersive couch according to an embodiment of the disclosure have been described above, they are merely an example and it will be understood by those skilled in the art that partial substitution and modification of the above-described embodiments can be made without departing from the technical spirit of the disclosure.

Therefore, the protection scope of the disclosure should be understood to affect the disclosure described in the appended claims and its equivalents.

INDUSTRIAL APPLICABILITY

According to the disclosure, an immersive couch according to the disclosure may be used as a motion chair, a simulator, etc. in the fields of simulation for games, driving, etc., appreciation for various images such as a stereoscopic image, and so on.

The invention claimed is:

1. An immersive couch comprising:
a couch body defined as an inflatable body;
a holding unit disposed on the couch body;
an actuation connecting member having one end connected to the holding unit;
a rotary body configured to wind and unwind the actuation connecting member;
a rotary body actuator configured to rotate the rotary body forwards and backwards; and
a controller configured to control operations of the rotary body actuator.

2. The immersive couch of claim 1, wherein
the couch body comprises a lower body seat allowing a lower body portion of a user to be seated thereon, and a backrest allowing an upper body portion of the user to be seated thereon, and
the actuation connecting member comprises a belt.

3. The immersive couch of claim 1, wherein
the rotary body actuator comprises an actuation motor, and a reducer to reduce a rotational force of the actuation motor, and
the rotary body comprises a pulley connected to an output shaft of the reducer.

4. The immersive couch of claim 1, further comprising:
an actuator housing in which the rotary body actuator and the rotary body are disposed; and
a supporting frame disposed in the actuator housing.

5. The immersive couch of claim 4, wherein
the actuator housing comprises a lower housing in which the rotary body actuator and the controller are disposed, and an upper housing coupled to an upper portion of the lower housing and defined with a moving hole through which the actuation connecting member moves, and
the supporting frame comprises a plurality of rod-shaped members disposed in the lower housing.

6. The immersive couch of claim 4, wherein
two rotary body actuators are positioned at rear left and right sides of the couch body to enable three-degree-of-freedom movements of the inflatable body, and
the holding unit comprises a planar body to be in close contact with the couch body, and a plurality of binding bands spaced apart from each other and disposed in edges of the planar body to be bound to the actuation connecting member and the supporting frame.

7. The immersive couch of claim 6, wherein
the plurality of binding bands comprise front binding bands extended from front left and right sides of the planar body and bounded to the supporting frame, and rear binding bands extended from rear left and right sides of the planar body and bounded to the actuation connecting member, and the front binding bands and the rear binding bands are bands, each having a structure that a width becomes narrower from an upper portion connecting with the planar body toward a lower portion.

\* \* \* \* \*